United States Patent [19]
Horstmann et al.

[11] Patent Number: 5,827,245
[45] Date of Patent: Oct. 27, 1998

[54] TRANSDERMAL THERAPEUTIC SYSTEM COMPRISING THE ACTIVE SUBTANCE 17-β-ESTRADIOL (ANHYDROUS)

[75] Inventors: Michael Horstmann, Neuwied; Marion Kursawe, Andernach; Horst Dzekan, Kleinmaischeid, all of Germany

[73] Assignee: LTS Lohmann Therapie-Systeme GmbH & Co. KG, Neuwied, Germany

[21] Appl. No.: 854,205

[22] Filed: May 9, 1997

Related U.S. Application Data

[63] Continuation of Ser. No. 367,356, Mar. 23, 1995, abandoned.

[30] Foreign Application Priority Data

Jul. 16, 1992 [DE] Germany ............... 42 23 360.7

[51] Int. Cl.⁶ .................. A61F 13/02; A61K 9/16
[52] U.S. Cl. .......................... 604/307; 424/449
[58] Field of Search .................. 604/289, 290, 604/307; 424/447, 448, 449; 128/888, 889; 602/41–59

[56] References Cited

U.S. PATENT DOCUMENTS

| | | | |
|---|---|---|---|
| 3,854,480 | 12/1974 | Zaffaroni . | |
| 4,792,484 | 12/1988 | Moritani | 428/323 |
| 4,842,864 | 6/1989 | Guillemet et al. | 424/448 |
| 4,863,738 | 9/1989 | Taskovich . | |
| 5,041,434 | 8/1991 | Lubkin | 514/182 |
| 5,047,244 | 9/1991 | Sanvordeker et al. | 424/448 |
| 5,079,008 | 1/1992 | Sinnreich et al. | 424/448 |
| 5,128,124 | 7/1992 | Fankhauser et al. | 424/449 |
| 5,128,138 | 7/1992 | Blank | 424/449 |

FOREIGN PATENT DOCUMENTS

| | | |
|---|---|---|
| 0 304 227 | 2/1989 | European Pat. Off. . |
| 0 337 358 | 10/1989 | European Pat. Off. . |
| 0 421 454 | 4/1991 | European Pat. Off. . |
| 9010425 | 9/1990 | WIPO . |
| WO 90/10425 | 9/1990 | WIPO . |

OTHER PUBLICATIONS

T. Higuchi, "Physical Chemical Analysis . . ." J. Soc. Cosmetic Chem. 11, pp. 85–97 (1960).

Busetta et Michel Hospital "Structure Cristalline . . ." Acta Cryst. 1972, B28, pp. 560–567.

Kuhnert–Brandstätter and H. Winkler (1976) Scientia Pharmaceutica 44 (3) pp. 177–190.

*Primary Examiner*—John G. Weiss
*Assistant Examiner*—David J. Cho
*Attorney, Agent, or Firm*—Collard & Roe, P.C.

[57] ABSTRACT

A transdermal therapeutic system containing the active substance 17-β-estradiol and optionally further active substances has a laminated structure positioned on a backing layer which is essentially impermeable to active substance and moisture, at least one matrix layer and optionally an adhesive layer. The at least one matrix layer or the adhesive layer contains anhydrous 17-β-estradiol in crystalline form.

15 Claims, 1 Drawing Sheet

TRANSDERMAL THERAPEUTIC SYSTEM COMPRISING THE ACTIVE SUBTANCE 17-β-ESTRADIOL (ANHYDROUS)

This is a continuation of application Ser. No. 08/367,356 filed on Mar. 23, 1995 now abandoned.

BACKGROUND OF THE INVENTION

1. Field of the Invention

The invention relates to a transdermal therapeutic system for the release of 17-β-estradiol and, optionally, further active substances through the skin to the human body.

2. The Prior Art

Transdermal therapeutic systems (TTS) have already been introduced on the market for the pharmaceutical therapy of a series of deseases. Meanwhile, even TTS comprising the active substance 17-β-estradiol have become available on the market as therapeutic agents for climacteric complaints, recently also for osteoporosis, and they are being successfully applied in therapy.

One disadvantage of the systems according to the prior art is the insufficient capacity of the active substance to permeate the skin, which despite numerous galenic measures aimed at the TTS design (the use of multilayered systems and control membranes, variation of the active substance concentration, modification of the base polymer, etc.) cannot be increased beyond a certain limit, the so-called "saturation flow". The conclusion that the transdermal flow of an active substance out of the solid, finely dispersed phase can in principal not be increased further, not even where more highly solvent vehicles are used, already appears in the works of Higuchi (e.g. T. Higuchi: Physical Chemical Analysis of percutaneous absorption process from creams and ointments. J. Soc. Cosmetic Chem. 11, pages 85–97 (1960), which have been pioneering books to this day.

The systems described in EP 0 421 454 contain 17-β-estradiol in an acrylate polymer with the addition of crystallization inhibitors and tackifying resins. The systems contain swelling substances for protection against premature loss of adhesiveness.

However, with many active substances there is a possibility to add so-called enhancers (penetration enhancers) to the TTS during the production. These are additives, which are generally liquid and which enhance the resorption properties of the human skin and thus permit resorption from a sufficiently small TTS area. Particularly highly volatile enhancers, such as ethanol, which is used for example for the active substance 17-β-estradiol, present problems of excessive softening of the adhesive layers of the TTS and, above all, make further space-consuming compartments necessary, which render the TTS unacceptably thick.

Furthermore, every additional non-polymeric additive involves a danger of intolerance to the skin, possibly also of sensitization.

However, when adding certain, less volatile enhancers (e.g. glycerol ester, cyclic amids, eucalyptol), which are, however, mostly less active, it is possible to produce matrix systems that contain the active substance and the resorption-enhancing component in one or more monolithic layers.

U.S. Pat. No. 4,863,738 is one of many examples claiming the application of active substances, e.g. 17-β-estradiol together with a particular enhancer (in this case glyceryl monooleate) in any desired TTS matrix and in any desired concentration.

Unfortunately, according to the state of the art, with such TTS a satisfactory therapy cannot be achieved either, since either the selected enhancers are too poorly tolerated by the skin, or the systems have an unacceptable large area owing to the still insufficient flow through the skin.

Another (theoretic) possibility to increase the active substance flow through the skin is to dissolve greater amounts of the active substance in the TTS as a molecular dispersion than corresponds to the saturation solubility. As the degree of oversaturation of such systems increases, the speed of the permeation through the skin increases accordingly. As such physical conditions are, however, thermodynamically unstable, pharmaceutic products of this kind cannot be stored. Within months or at the latest years, a spontaneous, unpredictable precipitation of active substance particles occurs, so that the flow rate through the skin gradually falls down to the saturation flow level, and thus a great part of the initially present therapeutic activity is lost.

SUMMARY OF THE INVENTION

It is the object of the present invention to provide a transdermal therapeutic system comprising the active substance 17-β-estradiol which exhibits higher active substance flows on the skin than systems according to the art comprising the same active substance, and which is protected against loss of activity caused by recrystallization (precipitation of active substances) during the period of storage (until the date by which the TTS must be used or consumed). A further object of the application is to provide a process suitable for the production of said TTS.

According to the invention, this object is achieved in a transdermal therapeutic system by the fact that at least one of the matrix layers and/or the adhesive layer contains anhydrous 17-β-estradiol in crystalline form. Production processes suitable for this purpose are provided.

At room temperature and usual relative humidity of air (20 to 60% relative humidity), 17-β-estradiol is not present in one of the two known modifications (I and II) which are free from crystal water but as a semihydrate (Busetti a. Hospital, Acta Cryst. 1972, B28, 560). Due to the stratified structure of the crystal compound, which is stabilized by hydrogen bridges, and its diffusion density, the hydrate can be heated for a short period of time to temperatures of about 170° C. (Kuhnert-Brandstätter u. Winkler (1976) Scientia Pharmaceutica 44 (3), 177–190) while remaining undecomposed. However, by way of micronization, i.e. increasing the surface of the crystals, it is possible to quantitatively convert 17-β-estradiol semihydrate to its anhydrous form at as low a temperature as about 120° C. According to our own observations, conversion already occurs at about 90° C. where heating is slow (0.2 to 1 K/min) and particularly fine material is used.

On the other hand, with decreasing water vapour partial pressure, 17-β-estradiol exhibits higher solubilities in some polymers, especially also in polyacrylates (example 1). The acrylic-acid ester copolymer has a solubility for the active substance anhydrous 17-β-estradiol of between 0.4 and 3.0% g/g.

Since, according to Fick's Law the diffusion flow through the skin increases with increasing concentration and under otherwise equal conditions, such an increase in concentration in transdermal therapeutic systems is very much desired. Unfortunately the water introduced with the 17-β-estradiol semihydrate is already sufficient to initiate a renewed, gradual crystallization of 17-β-estradiol semihydrate from the solution (Kuhnert-Brandstätter u. Winkler (1976) Scientia Pharmaceutica 44(3), 177–190). Following crystallization, unfortunately, the flow rate from the system to the skin also falls dramatically as the concentration decreases. Therefore, according to the invention, both a matrix which contains little water is prepared, by carefully drying the laminar components of the transdermal therapeutic system, and a thermodynamically stabilizing phase is incorporated or produced, for example by conversion from estradiol semihydrate. As this form is the energetically more unstable at room temperature, it exhibits a considerably higher solubility than the semihydrate—the result is thus a saturated solution containing solids remaining at the bottom, while having a free 17-β estradiol concentration which is clearly higher than that of systems prepared in environments with atmospheric moisture. As a matter of course, absolutely dry storage conditions are required in order to stabilize these properties. Such conditions can be achieved by utilizing gas- and moisture-tight packing materials or by putting one or more moisture-absorbing objects in the packing material.

The above-described use of anhydrous estradiol in crystalline form may according to the invention be realized in a TTS in various ways: The most simple form is a single-layered matrix system, the matrix of which at the same time also functions as a pressure-sensitive adhesive layer, thus making the adhesive layer superfluous. By means of the crystals contained in the matrix, the desired high free concentration of estradiol is maintained in equilibrium to the crystalline anhydrate. The delivery of active substance by gradual dissolution of the crystals ensures a constant active substance release owing to the constant thermodynamic activity.

If direct contact of the skin with the active substances is to be avoided, only the matrix (which is at a distance from the skin) is provided with 17-β-estradiol anhydrate crystals, and an adhesive layer which is near to the skin and free from particulate estradiol is applied by laminating.

If a membrane which is poorly penetratable for estradiol is inserted between such a matrix and the adhesive layer, the active substance release achieved is controlled more by the plaster than the skin.

Since the use of suspended micronized estradiol in the solvent mixtures commonly used for acrylic-acid ester copolymers (ethanol, ethylacetate, methyl ethyl cetone, etc.) results in high substance loss due to high solubility, the use of polymers which are soluble in petrol, such as polyisobutylene, can also be of particular advantage.

In all cases the presence of crystalline, i.e. particulate estradiol anhydrate, is characteristic for the transdermal therapeutic systems according to this invention. The exact portion of this pseudopolymorphic form of estradiol in the system is of no significance; what is decisive for the function is merely the presence of at least one to two crystals per square millimeter, so that the system is in equilibrium with the anhydrous crystalline estradiol and shows the advantages of increased active substance release.

The TTS according to this invention can be easily distinguished from systems according to the art by polarization-microscopic determination of estradiol crystals in the TTS and by the oversaturation of the surrounding medium with estradiol, which simultaneously occurs, at least temporarily, after immersion in water or buffer solution.

DETAILED DESCRIPTION OF PREFERRED EMBODIMENTS

Figure 1:
FIG. 1: System according to the invention
1—backing layer of polyester
2—estradiol anhydrate (anhydrous 17-β-estradiol)
3—matrix of styrene/isoprene/styrene copolymer and resin comprising a dissolved active substance portion
4 siliconized polyester film as protecting film
Figure 2:
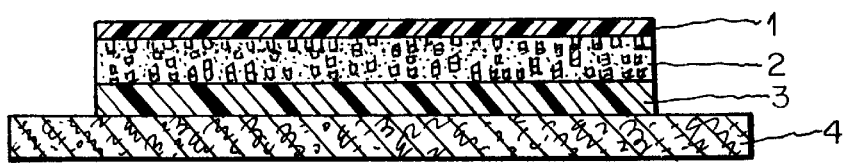
FIG. 2: System according to the invention
1—backing layer of polyester
2—estradiol anhydrate (anhydrous 17-β-estradiol)
3—acrylic-acid ester copolymer comprising a dissolved active substance portion
4—siliconized polyester film as protecting film
Figure 3:
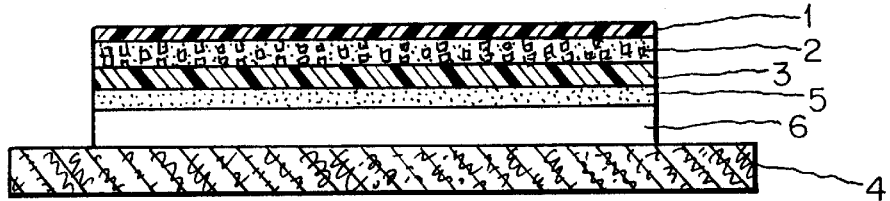
FIG. 3: System according to the invention
1—backing layer of polyester
2—estradiol anhydrate (anhydrous 17-β-estradiol)
3—acrylic-acid ester copolymer comprising a dissolved active substance portion
4—siliconized polyester film as protective film
5—EVA copolymer film
6—acrylic-acid copolymer as adhesive layer
Figure 4:
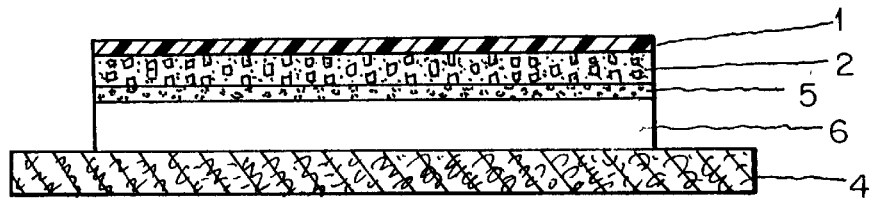
FIG. 4: System according to the invention
1—backing layer of polyester
2—estradiol anhydrate (anhydrous 17-β-estradiol)
3—acrylic-acid ester copolymer comprising a dissolved active substance portion
4—siliconized polyester film as protecting film
5—polyisobutylene comprising a dissolved active substance portion
6 acrylic-acid ester copolymer as adhesive layer

The invention will be illustrated by the following examples:

EXAMPLE 1

To determine the influence of different moistures of water vapour on the solubility of 17-β-estradiol, first the following active substance-free, tacky layers were used (layer thickness in all cases about 80 micrometers)
A. acrylate polymer 1 without additive
B. acrylate polymer 1 with 12% (g/g) oleic acid
C. acrylate polymer 1 with 5% ethyl laureate
D. acrylate polymer 2 without additive
E. acrylate polymer 3 without additive
F. acrylate polymer 4
G. acrylate polymer 4 with 10% isopropyl palmitate
H. acrylate polymer 5
I. mixture of 3 parts by weight of styrene/isoprene-styrene blockcopolymer and 7 parts by weight of a colophony rosin ester having a softening temperature of 85° C.

For testing, a test film of silicone rubber containing 8%-wt. of micronized 17-β-estradiol (thickness 50 micrometers) is used.

If punched-out portions (circular, 5 cm$^2$) of the aforementioned plastic films are each applied onto one 10-cm$^2$-large punched-out portion of the silicone suspension carrier in such a manner that air bubbles do not occur and 17-β-estradiol can diffuse from the silicone rubber/estradiol suspension into the adhesive matrix, the portion of 17-β-estradiol diffusing into the applied film after storage for about two weeks is substantially only determined by the saturation solubility in the test polymer.

The saturation solubility is altered by means of experimental environment conditions as follows:

The samples are sealed, together with the required humidity controlling device (see below), in a sealable composite packing material (paper/aluminium/ethylene vinyl acetate) and stored at 21° C./60% for at least 10 days.

Humidity controllers 1. 95% relative humidity: inserted strip of nonwoven, impregnated with sodium hydrogenphosphate solution, saturated 2. 65% relative humidity: inserted strip of nonwoven, impregnated with sodium nitrite solution, saturated 3. 0% relative humidity: about 10 grains of blue gel, about 1 g The resulting number of individual samples is thus 10×3= 30.

Immediately prior to measuring, the silicone carrier must be removed from the samples A–I.

Measurement

All of the 27 samples are put into screw cap jars containing 100 ml of 0.9% sodium chloride solution and after a total period of 5 h the experiment is concluded and samples taken.

The estradiol content of the samples is determined by means of HPLC with UV-detection; the resulting estradiol content eluted from the matrix pieces is as follows:

| Rel. Humidity: | 0% | 65% | 95% |
| --- | --- | --- | --- |
|  | estradiol content | | |
| A | 0.41% | 0.24% | 0.25% |
| B | 0.38% | 0.23% | 0.19% |
| C | 0.38% | 0.20% | 0.18% |
| D | 0.42% | 0.26% | 0.26% |
| E | 0.39% | 0.30% | 0.34% |
| F | 0.30% | 0.22% | 0.20% |
| G | 0.28% | 0.15% | 0.16% |
| H | 0.54% | 0.27% | 0.32% |
| I | 0.06% | 0.03% | 0.05% |

The measured values in most cases show a considerably higher solubility for dry storage. As the storage period was relatively short and estradiol semihydrate was used instead of anhydrous estradiol, it must be assumed that the increase in solubility can be raised further by dry conditions.

EXAMPLE 2

Preparation of a System According to the Invention 2.0 17-β-estradiol semihydrate, micronized
60.0 g Cariflex® TR 1107 (styrene-isoprene-styrene blockcopolymer)
138.0 g Foral® 85 (thermoplastic ester resin of colophonium derivatives)
200.0 g petrol (boiling range of 80° to 100° C.)
are stirred in a cylindrical glass vessel at room temperature until a homogeneous suspension is obtained and thereafter coated by means of a continuously operating coating machine on a siliconized polyester film having a thickness of 100 micrometers, such that a layer thickness of 100 g/m$^2$ (relative to the solvent-free portion) results.

The coatings are each dried for 2.4 min at 40° C., 60° C., 80° C. and at 120° C. 15 micrometer-thick polyester film is then immediately applied to (laminated on) the dried layer under roll pressure, so that no air bubbles remain.

By punching with a wad punch, transdermal systems of 16 cm$^2$ are obtained, which were tested according to example 5.

EXAMPLE 3

Preparation of a System According to the Prior Art 2.0 g 17-β-estradiol semihydrate, micronized
60.0 g Cariflex® TR 1107 (styrene-isoprene-styrene block copolymer)
138.0 g Foral® 85 (thermoplastic ester resin of colophonium derivatives)
200.0 g petrol (boiling range 80° to 100° C.)
are stirred in a cylindrical glass vessel at room temperature until a smooth suspension is obtained and thereafter coated by means of a continuously operating coating machine on a siliconized polyester film having a thickness of 100 micrometers, such that a layer thickness of 100 g/m$^2$ (relative to the solvent-free portion) results.

The coatings are each dried for 3.6 min at 40° C. and 60° C. and for 7.2 min at 70° C.

15 micrometer-thick polyester film is then immediately applied to (laminated on) the dried layer under roll pressure, so that no air bubbles remain. By punching with a wad punch, transdermal systems of 16 cm$^2$ are obtained, which were packed in composite packing material of paper/aliminium foil/heat sealable layer and tested after more than two weeks according to example 5.

EXAMPLE 4

Determination of release in vitro

The release of the transdermal therapeutic system is determined by the "paddle-over-disc" method of the United States Pharmacopeia (USP). For this purpose, the TTS (16 cm$^2$) is coated with 500 ml buffer solution (pH 7.4).

During the measurement, a paddle stirrer continuously moves against the system at 150 min$^{-1}$. After 3.8 and 24 hours, samples of the buffer solution are taken and the estradiol content of the samples (relative to estradiol semihydrate) is checked by HPLC.

The measured values were as follows:

|  | Released quantity of estradiol (mg) | | |
| --- | --- | --- | --- |
| TTS No. | 3h | 8h | 24h |
| Systems according to Example 2: | | | |
| 1 | 0.106 | 0.178 | 0.338 |
| 2 | 0.117 | 0.208 | 0.324 |
| 3 | 0.109 | 0.190 | 0.328 |
| 4 | 0.114 | 0.187 | 0.331 |
| Systems according to Example 3 (comparison example according to the art) | | | |
| 1 | 0.077 | 0.119 | 0.179 |
| 2 | 0.076 | 0.128 | 0.183 |
| 3 | 0.079 | 0.135 | 0.202 |
| 4 | 0.072 | 0.122 | 0.183 |

EXAMPLE 5

Determination of permeation through animal skin in vitro

In a skin permeation cell of glass having an acceptor volume of 20 ml and which is thermostatted at 37° C. and has 2.54 cm$^2$ of free diffusion area, a sufficiently large piece of excised hairless mouse skin is stretched, which is flown against by the acceptor medium on its lower side and onto whose upper side (corneum) the TTS to be tested has previously been stuck.

After 8 and after 24 hours the medium is replaced and the estradiol content thereof is determined by HPLC.

More than two weeks prior to the measurement the TTS were each packed in a sealed bag containing 1 g of predried silica gel in order to exclude the influence of air humidity during storage.

The resulting measured values were as follows (released estradiol in microgrammes per cm$^2$):

| TTS according to | Time | | Storage |
| --- | --- | --- | --- |
| | 8 hours | 24 hours | |
| Example 2 | 1.7 | 4.3 | without |
| Example 3 (comparison) | 1.2 | 2.4 | without |
| Example 2 | 1.8 | 4.8 | with |
| Example 3 (comparison) | 0.7 | 3.1 | with dehumidifier |

The TTS comprising the active substance 17-β-estradiol in crystalline form also differs from preparations containing the same active substance in form of a semihydrate in that during storage prior to application it is present in a gas-tight, sealed packing material together with a dehydrating or water-absorbing agent.

We claim:

1. A transdermal therapeutic system comprising a laminated structure positioned on a backing layer which is substantially impermeable to an active substance and to moisture;

at least one matrix layer within said laminated structure and which contains anhydrous 17-β-estradiol in crystalline form; and said system, during storage prior to application, is present in combination within a gas-tight, sealed packing material containing a dehydrating water-absorbing substance; and crystals of said anhydrous 17-β-estradiol in the matrix layer are in equilibrium with dissolved 17-β-estradiol, whereby a high concentration of dissolved estradiol is maintained in equilibrium to the crystalline form by gradual dissolution of the crystals owing to constant thermodynamic activity.

2. The transdermal therapeutic system according to claim 1, wherein said at least one matrix layer contains 17-β-estradiol in crystalline and anhydrous form; and further comprising a skin-facing pressure sensitive adhesive layer which is free from crystalline 17-β-estradiol.

3. The transdermal therapeutic system according to claim 2, wherein the adhesive layer has a base material which is an acrylic-acid ester copolymer.

4. The transdermal therapeutic system according to claim 1, wherein the at least one matrix layer has a base material which is polyisobutylene.

5. The transdermal therapeutic system according to claim 1, wherein the at least one matrix layer has a base material which is an acrylic-acid ester copolymer.

6. The transdermal therapeutic system according to claim 3, wherein the acrylic-acid ester copolymer has a solubility for the active substance anhydrous 17-β-estradiol of between 0.4 and 3.0% g/g.

7. The transdermal therapeutic system according to claim 5, wherein the acrylic-acid ester copolymer has a solubility for the active substance anhydrous 17-β-estradiol of between 0.4 and 3.0% g/g.

8. The transdermal therapeutic system according to claim 1, wherein the active substance 17-β-estradiol in crystalline form is present in a gas-tight, sealed packing material together with a dehydrating water-absorbing substance.

9. A transdermal therapeutic system comprising a laminated structure positioned on a backing layer which is substantially impermeable to an active substance and to moisture;

at least one matrix layer within said laminated structure and which contains anhydrous 17-β-estradiol in crystalline form; and said system, during storage prior to application, is present in combination within a gas-tight, sealed packing material containing a dehydrating water-absorbing substance.

10. The transdermal therapeutic system according to claim 9, comprising wherein said at least one matrix layer contains 17-β-estradiol in crystalline and anhydrous form; and further comprising a skin-facing pressure sensitive adhesive layer which is free from crystalline 17-β-estradiol.

11. The transdermal therapeutic system according to claim 10, wherein the at least one matrix layer has a base material which is an acrylic-acid ester copolymer.

12. The transdermal therapeutic system according to claim 9, wherein the at least one matrix layer has a base material which is polyisobutylene.

13. The transdermal therapeutic system according to claim 9, wherein the at least one matrix layer has a base material which is an acrylic-acid ester copolymer.

14. The transdermal therapeutic system according to claim 11, wherein the acrylic-acid ester copolymer has a solubility for the active substance anhydrous 17-β-estradiol of between 0.4 and 3.0% g/g.

15. The transdermal therapeutic system according to claim 13, wherein the acrylic-acid ester copolymer has a solubility for the active substance anhydrous 17-β-estradiol of between 0.4 and 3.0% g/g.

* * * * *